United States Patent [19]

Baldwin et al.

[11] 4,279,913

[45] Jul. 21, 1981

[54] POLYSUBSTITUTED-2-(3-LOWERALK-YLAMINO-2-R$_1$O-PROPOXY)PYRIDINES

[75] Inventors: John J. Baldwin; Gerald S. Ponticello, both of Lansdale, Pa.

[73] Assignee: Merck & Co., Inc., Rahway, N.J.

[21] Appl. No.: 7,092

[22] Filed: Jan. 29, 1979

Related U.S. Application Data

[63] Continuation-in-part of Ser. No. 866,961, Jan. 4, 1978, abandoned.

[51] Int. Cl.$^3$ ............... C07D 215/20; C07D 221/04; A61K 31/44; A61K 31/47
[52] U.S. Cl. .................... 424/258; 424/263; 546/112; 546/157; 546/281; 546/288; 546/297; 546/298; 546/145
[58] Field of Search ............... 546/288, 112, 281, 300, 546/297, 298, 145, 157; 424/263, 258

[56] References Cited

U.S. PATENT DOCUMENTS

| 3,946,009 | 3/1976  | Wasson et al. | 260/247.5 D |
| 4,000,282 | 12/1976 | Baldwin       | 424/263     |
| 4,053,605 | 10/1977 | Baldwin       | 424/263     |
| 4,060,601 | 11/1977 | Baldwin       | 424/263     |
| 4,065,461 | 12/1977 | Ross-Petersen | 546/297     |

FOREIGN PATENT DOCUMENTS

| 2507902 | 10/1975 | Fed. Rep. of Germany | 546/298 |
| 1305644 | 2/1973  | United Kingdom       | 260/465 |
| 1465946 | 3/1977  | United Kingdom       | 544/124 |

OTHER PUBLICATIONS

Gnewuch et al., J. Med. Chem., vol. 15, pp. 1321–1323, (1972).
Fitzgerald, Clin. Pharmacol. Ther., vol. 10, pp. 292–306 (1969).
Baldwin et al., J. Org. Chem., vol. 43, pp. 2529–2535, (1978).
Sperber et al., J.A.C.S., vol. 81, pp. 704–709, (1959).

*Primary Examiner*—Alan L. Rotman
*Attorney, Agent, or Firm*—Daniel T. Szura; Harry E. Westlake, Jr.

[57] ABSTRACT

Novel substituted (3-loweralkylamino-2-R$_1$O-propoxy)-pyridines, their pharmaceutically acceptable salts, certain intermediates and their preparation are disclosed. These pyridines have pharmaceutically useful properties such as $\beta$-adrenergic blocking activity.

9 Claims, No Drawings

POLYSUBSTITUTED-2-(3-LOWERALKYLAMINO-2-R₁O-PROPOXY)PYRIDINES

CROSS REFERENCE TO RELATED APPLICATIONS

This application is a continuation in part of U.S. Application Ser. No. 866,961 filed Jan. 4, 1978, now abandoned.

BACKGROUND OF THE INVENTION

The present invention concerns substituted (3-loweralkylamino-2-$R_1$O-propoxy)pyridines having pharmaceutically useful properties.

β-Adrenergic blocking agents or β-blockers are known to be useful in treating certain cardiovascular disorders such as arrhythmia, angina pectoris. While these β-blockers can also have antihypertensive activity, the onset of this activity is generally gradual. The structure and activity of β-blockers is generally discussed in "Clinical Pharmacology and Therapeutics" 10, 292, 306 (1969). Substituted N-heteroaryl β-adrenergic blocking agents are disclosed in British Pat. No. 1,305,644, U.S. Pat. No. 4,000,282, U.S. Pat. No. 3,946,009, Journal of Medicinal Chemistry 16, 1113-1114 (1973) and Journal of Medicinal Chemistry 15, 1321 (1972).

Novel substituted (3-loweralkylamino-2-$R_1$O-propoxy)pyridines have been discovered. These compounds have β-adrenergic blocking activity; some compounds also have antihypertensive activity of immediate onset.

SUMMARY OF THE INVENTION

Novel substituted (3-loweralkylamino-2-$R_1$O-propoxy)pyridines and their pharmaceutically acceptable salts which have β-adrenergic blocking activity and certain intermediates and their preparation.

DESCRIPTION OF THE PREFERRED EMBODIMENTS

An embodiment of the present invention is compounds having the formula

I $R_3$, $R_4$ substituted pyridine with $R_2$, $OR_1$, $O-CH_2-CH-CH_2-NHR$

II

N-(CH$_2$)$_n$ substituted pyridine with $R_2$, $OR_1$, H, $O-CH_2-CH-CH_2-N-R$ wherein
n is 3, 4, 5 or 6,
R is $C_3-C_4$ branched alkyl,
$R_1$ is H or $$-\overset{O}{\underset{\|}{C}}-L$$

wherein L is selected from $C_1-C_{10}$ alkyl, phenyl and substituted phenyl having up to two substituents which are independently selected from $C_1-C_4$ alkyl, $C_1-C_4$ alkoxy and halo, $R_2$ is F, CN, $CF_3$, Cl, $-N\overbrace{\phantom{xxx}}$ , $NO_2$, $-COOR_5$ wherein $R_5$ is H, $C_1-C_6$ alkyl or $C_6-C_{12}$ carbocyclic aryl, $-CONR_6R_7$ wherein $R_6$ and $R_7$ when separate, are H or $C_1-C_6$ alkyl and when joined, are $-CH_2-(CH_2)_3-CH_2$, $-CH_2-CH_2-O-CH_2-CH_2-$, $-CH_2-CH_2-NH-CH_2-CH_2-$, or $-CH_2-CH_2-N(CH_3)-CH_2-CH_2-$, and $R_3$ and $R_4$ are independently selected from H, $C_1-C_4$ alkyl, $CF_3$, F, $-N\overbrace{\phantom{xxx}}$ , $C_1-C_4$ $$\text{alkyl}-\overset{O}{\underset{\|}{C}}-NH,$$

formyl, $C_1-C_4$ alkylester, COOH, phenyl and substituted phenyl having up to two substituents which are independently selected from $C_1-C_4$ alkyl, $C_1-C_4$ alkoxy and halo, such that one of $R_3$ and $R_4$ is other than H,
and pharmaceutically acceptable salts thereof.

$R_1$ is H or the $$-\overset{O}{\underset{\|}{C}}-L \text{ group,}$$

with H being preferred. The L group includes $C_1-C_{10}$, linear and branched hydrocarbon alkyl such as methyl, n-decyl, tert butyl, isoamyl, n-heptyl and the like with $C_1-C_4$ alkyl being preferred, and phenyl or mono- and disubstituted phenyl such as tert butylphenyl, 2,6-dibromophenyl, 3-methylphenyl, 4-n-propylphenyl, 3,5-dimethoxyphenyl, 4-iodophenyl, 2-methyl-4-chlorophenyl, 4-fluorophenyl and the like, with monosubstituted phenyl preferred.

The $R_2$ ester groups are $C_1-C_6$ alkylester exemplified by $-COOCH_3$, $-COOC_6H_{13}$, $-COOCH(CH_3)_2$, $-COOC_2H_5$ and the like and $C_6-C_{12}$ carbocyclic aryl ester exemplified by $C_6H_5-OOC$, p-$CH_3-C_6H_4-OOC-$, $C_6H_5-C_6H_4-OOC-$, $C_{10}H_7-OOC-$ and the like; and the amide groups include $-CONH_2$, $C_1-C_6$ substituted amide groups such as $-CON(CH_3)_2$, $-CON(C_6H_{13})_2$, $-CONHC_2H_5$, $-CON$(sec butyl)$_2$ and the like and carbonyl heterocyclic groups such as

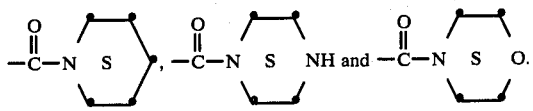

The R3/R4 C1–C4 alkyl substituent include the branched and unbranched hydrocarbon moieties e.g. CH3, isopropyl, n-propyl etc.; the substituted phenyl groups include mono or disubstituted phenyls such as p-tolyl, 2,6-dibromophenyl, 4-isopropylphenyl, 3,5-dimethoxyphenyl, 2-fluorophenyl, 2-methyl-4-chlorophenyl, 3-chlorophenyl, 4-iodophenyl and the like, monosubstituted phenyl being preferred; and the C1–C4 alkyl-CONH groups include CH3CONH, (CH3)3—C—CONH, C2H5—CONH and the like.

R is isopropyl, sec butyl, or test butyl with tert butyl being preferred.

The alkylene moiety bridging positions 4–5 in Formula II may have from 3–6 units. The —CH2—CH2—CH2— and —CH2—(CH2)2—CH2— groups are preferred.

Examples of compounds of Formula I are
2-(3-tert-butylamino-2-hydroxypropoxy)-3-trifluoromethyl-4-methylpyridine,
2-(3-isopropylamino-2-hydroxypropoxy)-3-cyano-5-acetamidopyridine,
2-(3-tert butylamino-2-hydroxypropoxy)-3-trifluoromethyl-5-methylpyridine,
2-(3-sec butylamino-2-hydroxypropoxy)-3-(1-pyrrolyl)-5-trifluoromethyl pyridine,
2-(3-R-amino-2-OR1-propoxy)-3-cyano-4-phenyl-5-methylpyridine,
2-(3-tert butyl-2-hydroxypropoxy)-3-cyano-4-phenylpyridine and the like.

Examples of Formula II compounds are

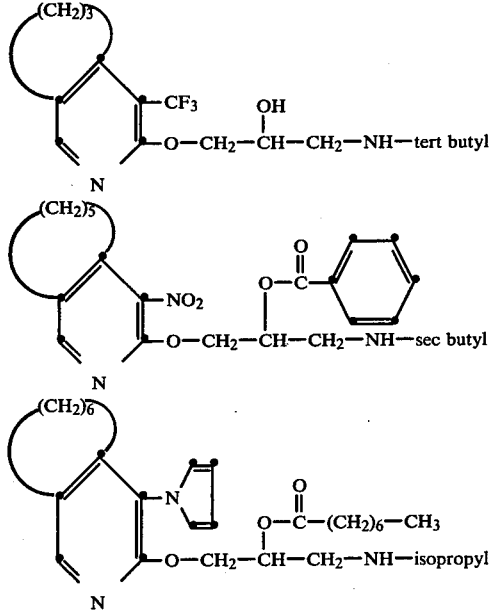

and the like.

A class of preferred compounds are those having the formula

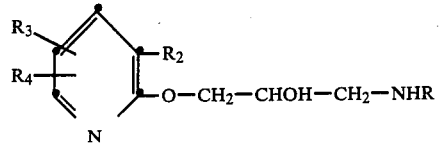

Another class of preferred compounds are those of Formula I where R4 is H. These compounds have the formula

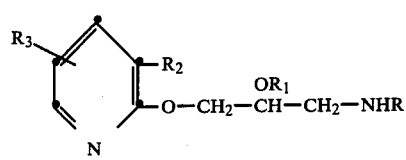

where R, R1, R2 and R3 are as defined above. Preferred R3 substituents are CN, CF3, 1-pyrrolyl, Cl, F, phenyl, CH3 or C2H5. The compounds of Formula IV where R3 is in the 4 or 5 position are more preferred and where R1 is H and R is tert butyl, the compounds are more particularly preferred. Especially preferred compounds of Formula IV are those wherein additionally R2 is —CN, F or CF3 and most preferably CN or F.

Examples of the compounds of Formula IV are
2-(3-sec butylamino-2-hydroxypropoxy)-3-cyano-4-ethylpyridine,
2-(3-isopropylamino-2-hydroxypropoxy)-3-fluoro-4-methylpyridine,
2-(3-tert butylamino-2-hydroxypropoxy)-3-trifluoromethyl-4-fluoropyridine,
2-(3-isopropylamino-2-benzoyloxypropoxy)-3-(1-pyrrolyl)-5-methylpyridine,
2-[3-sec butylamino-2-(p-chlorobenzoyloxy)propoxy]-3-cyano-5-(1-pyrrolyl)pyridine,
2-(3-tert butylamino-2-hydroxypropoxy)-3-fluoro-4-phenylpyridine,
2-(3-isopropylamino-2-undecanoyloxypropoxy)-3-trifluoromethyl-5-ethylpyridine,
2-[3-tert butylamino-2-(p-methoxybenzoyloxy)propoxy]-3-fluoro-4-trifluoromethylpyridine,
2-[3-sec butylamino-2-(m-chlorobenzoyloxy)propoxy]-3-cyano-4-fluoropyridine,
2-[3-isopropylamino-2-(2-bromo-4-methylbenzoyloxy)propoxy]-3-cyano-5-(1-pyrrolyl)pyridine,
2-[3-tert butylamino-2-(3,5-dimethoxybenzoyloxy)propoxy]-3-trifluoromethyl-5-fluoropyridine,
2-(3-tert butylamino-2-hydroxypropoxy)-3-fluoro-4-ethylpyridine,
2-(3-isopropylamino-2-octanoyloxypropoxy)-3-fluoro-5-trifluoromethylpyridine,
2-(3-tert butylamino-2-isovaleryloxypropoxy)-3-chloro-5-trifluoromethylpyridine
and the like.

Another class of preferred compounds are those of Formula II. More preferred Formula II compounds are those wherein n is 3 or 4, more preferably when R2 is CN or F, and most preferably when R2 is CN, R1 is H and R is tert butyl.

The substituted pyridines of the present invention include all the optical isomer forms, that is mixtures of enantiomers e.g. racemates as well as the individual enantiomers. These individual enantiomers are commonly designated according to the optical rotation they effect, by (+) and (−), (L) and (D), (l) and (d) or combinations of these symbols. The symbols (S) and (R) stand for sinister and rectus respectively and designate an absolute spatial configuration of the enantiomer. The (S) isomer is a preferred isomer configuration.

The pyridines of the present invention can be prepared by any convenient process.

One such process involves the coupling of a halopyridine with a suitable substituted oxazolidine and hydrolyzing the reaction product obtained. This process is illustrated by the following set of reaction equations:

Reaction A

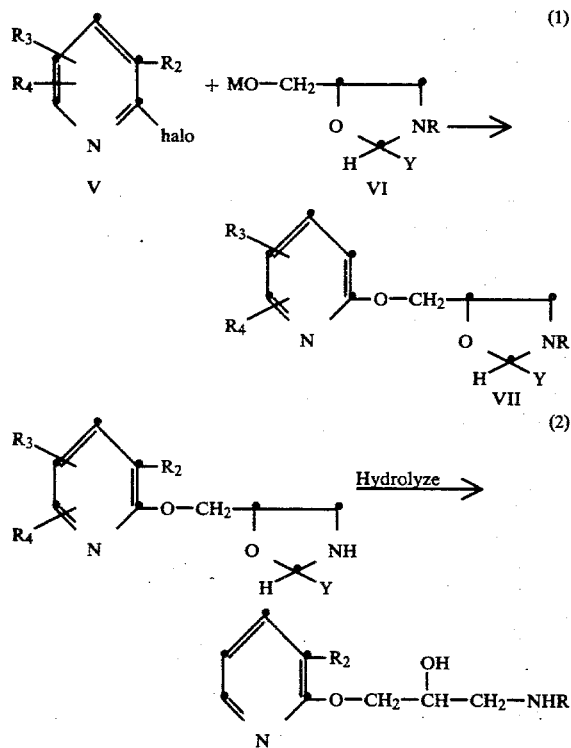

Halo may be Cl, Br and I, with Cl being preferred. M is an alkali metal, either potassium or sodium. Y can be hydrogen or the residue of any suitable aldehyde

e.g. an arylaldehyde, such as benzaldehyde, naphthaldehyde and the like, or a alkanal such as acetaldehyde, butyraldehyde and the like. The process for preparing oxazolidines where M is hydrogen is disclosed in U.S. Pat. Nos. 3,718,647 and 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this Reaction A may also be carried out with in-situ formation of the alkali metal oxazolidine salt (Formula VI) by reacting the oxazolidine

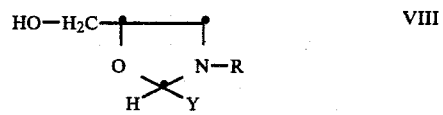

with the Formula V pyridine in the presence of a strong base such as an alkali metal alkoxide (e.g. K—O—C—(CH$_3$)$_3$) or sodium hydride.

The coupling reaction can be carried out at temperatures ranging from about 0° C. to the reflux temperature of the solvent. A temperature range of about 10° C. to about 75° C. is preferred. The reaction is generally carried out in a solvent. Any suitable solvent may be used. Examples of useful solvents are dimethylformamide, dimethylsulfoxide, hexamethylphosphoramide, tert butanol, alkanols and the like. The hydrolysis is carried out using conventional acid hydrolysis reagent and techniques e.g. treatment with a solution of an acid such as acetic acid or any strong mineral acid such as HCl or H$_2$SO$_4$. The hydrolysis product can be directly obtained as the salt of the acid used for the hydrolysis. Ordinarily, the product I is recovered as the free base after conventional neutralization of the salt.

The coupling reaction is ordinarily carried out at atmospheric pressure. Higher pressures may be used if desired.

When a racemic oxazolidine (Formula VI or VIII) is used as a reactant, the product is obtained as a racemate. The racemate may be separated into its individual enantiomers by conventional resolution techniques.

When Y in the oxazolidine e.g. (Formula VI or VIII) is other than hydrogen, in addition to the chiral center at oxazolidine position 5 there is a second chiral center at position 2. However, whenever the oxazolidine is designated e.g. as (S), (R) or (R,S), this designation refers only to the optical configuration around the carbon atom at the 5 position.

By using a single optical isomer of said oxazolidine in the above reactions, the product may be obtained directly as a single enantiomer. Thus, if the S-isomer of the oxazolidine is used, then the product obtained will be the S-isomer. This provides a convenient way for directly preparing individual isomers of the present invention.

The intermediates of Formula V may be prepared by any conventional process. Especially useful processes involve the condensation of alkylidenemalononitriles or alkyledinecyanoacetates with either HC(OC$_2$H$_5$)$_3$ or dimethylformamide dimethylacetal

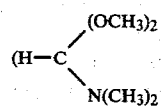

and cyclizing the unsaturated intermediate product with acid to provide Formula V compounds. These especially useful processes are an extension of the processes described by Bryson et al in J. Org. Chem. 41 2066 (1976) and J. Org. Chem. 39, 3436 (1974). The aforesaid malononitriles and cyanoacetates are prepared by methods available in the literature.

The following reaction equations illustrate the condensation reactions:

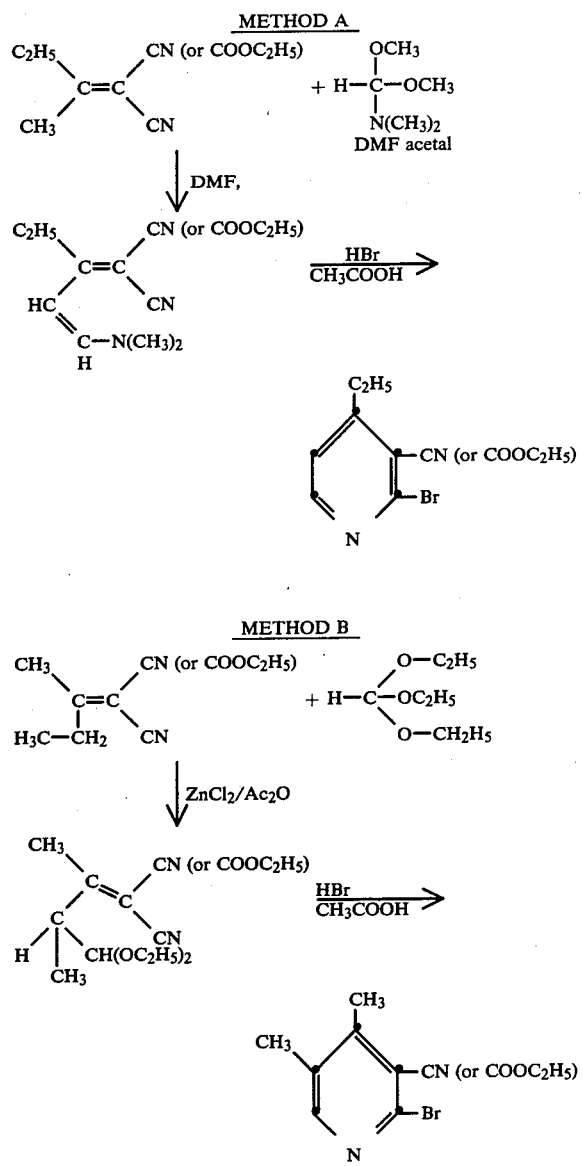

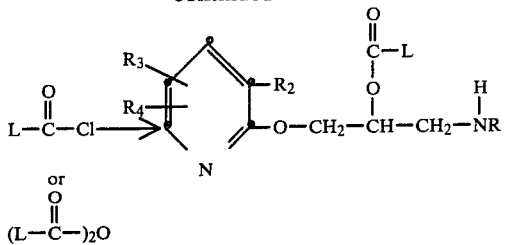

The intermediate pyridines of Formula V having a CF₃ substituent are obtained by hydrolyzing the ester group to the acid (COOH) and treating this derivative with a fluorinating agent e.g. SF₄/HF to obtain the CF₃ group.

Pyridines of the present invention wherein $R_1$ is other than hydrogen are conveniently prepared by treating the corresponding pyridine where $R_1$ is hydrogen with an appropriate acylating agent such as an acyl halide, e.g. undecanoyl chloride, pivaloyl chloride, benzoylchloride, p-methoxybenzoyl chloride, an anhydride e.g. acetic anhydride, and the like. The reaction is illustrated by the following equations:

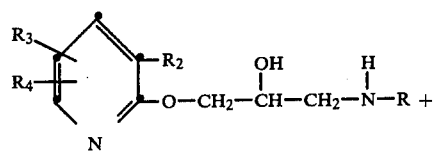

-continued

The compounds of the present invention also include the pharmaceutically acceptable salts of the novel pyridines. These salts are generally salts of the Formula I or II pyridines and organic or inorganic acids. These salts are prepared by treating the pyridine with an appropriate amount of a useful acid, generally in a suitable solvent. Examples of useful organic acids are isethionic acid and carboxylic acids such as maleic acid, acetic acid, tartaric acid, propionic acid, fumaric acid, succinic acid, pamoic acid, oxalic acid, pivalic acid and the like; useful inorganic acids are hydrohalo acids such as HCl, HBr, HI; sulfuric acid, phosphoric acid and the like. The hydrochloride and hydrogen maleate salts are examples of preferred salts.

The compounds of the present invention have β-adrenergic blocking activity. This activity is useful in treating cardiovasculer related disorders such as angina pectoris, arrhythmia, tachychardia etc. This β-adrenergic blocking activity may also be manifested in an antihypertensive effect of gradual onset after extended administration of the pyridine compound.

The β-adrenergic blocking activity of the present pyridine is determined by measuring the ability of represenative pyridines to block the β-adrenergic stimulant effect of isoproterenol.

Some of the present pyridines also exhibit antihypertensive activity of immediate onset This antihypertensive activity is believed to be the result of peripheral vasodilation via a mechanism not directly related to β-adrenergic blockade.

This rapid onset antihypertensive activity is determined by administering a representative pyridine of the present invention to spontaneously hypertensive (SH) rats and measuring the effect on blood pressure. Examples of representative compounds having this immediate onset antihypertensive activity are (S) 2-(3-tert butylamino-2-hydroxypropoxy)-3-fluoro-5-trifluoromethylpyridine, (S) 2-(3-tert butylamino-2-hydroxypropoxy)-3-cyano-5-(1-pyrrolyl)pyridine, (S) 2-(3-tert butylamino-2-hydroxypropoxy)-3-cyano-5-methylpyridine and (S) 2-(3-tert butylamino-2-hydroxypropoxy)-3-trifluoromethyl-5-fluoropyridine.

The observed β-adrenergic blocking activity of the present pyridines in test animals indicates that they are useful in humans as β-adrenergic blocking agents. The ability of certain of the present pyridines to reduce blood pressure, in an SH rat, rapidly and for extended duration, also indicates that the present pyridines are useful to treat hypertension in humans.

For use as β-adrenergic blocking agents, and/or antihypertensive agents the compounds of the present invention can be administered orally, by inhalation, by suppository or parenterally i.e. intravenously, intraperitoneally, etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material; or (2) for parenteral administration, dissolved, dispersed, or emulsified in a suitable liquid carrier or diluent or (3) as an aerosol or (4) as a suppository. The ratio of active ingredient (present pyridine) to compounding ingredients will vary as the dosage form requires. Conventional procedures are used to prepare the pharmaceutical formulations.

The dosage level for the present compounds may be varied from about 0.01 mg. to about 50 mg. per kilogram of animal body weight per day. Daily doses ranging from about 0.04 to about 2.5 mg/kg are preferred, with about 0.08 to about 1.25 mg/kg being a more preferred range. Oral administration if preferred. Either single or multiple daily doses may be administered depending on unit dosage.

Thus, another embodiment of this invention is a pharmaceutical composition containing β-adrenergic blocking or antihypertensive amount of a compound of the present invention.

The following examples illustrate the Method A and B preparations and conversion of the ester to the CF$_3$ derivative. Temperatures are in °Celsius.

EXAMPLE 1

METHOD A - Preparation of
2-Bromo-3-trifluoromethyl-5-methylpyridine a. To a solution of ethylpropylidene cyanoacetate (11.4 g, 0.074 m) in absolute ethanol (75 ml) was added DMF acetal (8.9 g, 0.074 m). After the addition, the solution was heated at reflux for 6 hours and then concentrated to dryness to yield 16.0 grams of crude 2-cyano-5-(N,N-dimethylamino)-4-methyl-2,4-pentanedienoate.

b. The crude 2-cyano-5-(N,N-dimethylamino)-4-methyl-2,4-pentanedienoate (15.9 g) was dissolved in acetic acid (50 ml) and the mixture heated at 40°. A solution of 30% HBr/acetic acid (100 ml) was added dropwise and then the mixture was heated to 55° with stirring. After heating for ¾ of an hour, the solution was poured onto ice, neutralized with solid Na$_2$CO$_3$ and extracted with CH$_2$Cl$_2$ (4×200 ml). The organic extracts were dried over Na$_2$SO$_4$, filtered and concentrated to dryness. The residue was distilled at 114°–120° (0.4 mm) to yield 6.3 g (35% yield) of ethyl 2-bromo-5-methylnicotinate c. A mixture of ethyl 2-bromo-5-methylnicotinate (7.1 g, 0.03 m) and 10% NaOH solution (500 ml) was heated on a stream bath with stirring. After 3 hours, the solution was cooled and neutralized with 12 N HCl. After cooling in an ice bath, the mixture was filtered to yield 5.6 g (39% yield) of 2-bromo-5-methylnicotinic acid.

The 2-bromo-5-methylnicotinic acid (5.0 g, 0.023 m), SF$_4$ (31 g; 0.020 m) and HF (5.3 ml) were charged to a steel bomb. The contents were heated at 120° for 8 hours. After cooling to room temperature, the bomb was opened and the contents poured into saturated Na$_2$CO$_3$ solution and extracted with CHCl$_3$ (3×100 ml). The organic layer was dried over Na$_2$SO$_4$, filtered and concentrated to dryness. The residue distilled at 45°–49° (0.1 mm) to yield 4 g (59% yield) of 2-bromo-3-trifluoromethyl-5-methylpyridine.

EXAMPLE 2

METHOD B - Preparation of
2-Bromo-3-cyano-5-methylpyridine a. A mixture of 1-propylidenemalononitrile (11.3 g, 0.104 m), acetic anhydride (21 ml), HC(OEt)$_3$ (16.3 g, 0.11 m) and ZnCl$_2$ (100 mg) was heated overnight at 145°. After 18 hours, the volatiles were removed by distillation at atmospheric pressure, acetic anhydride (5 ml) and HC(OC$_2$H$_5$)$_3$ (4 ml.) were added and the mixture heated at 150°. After 10 hours, the solution was cooled and added to saturated Na$_2$CO$_3$ solution. The aqueous solution was extracted with CHCl$_3$ (3×100 ml). The organic layer was dried over Na$_2$SO$_4$, filtered and concentrated to dryness. The residue distilled at 138°–158° (0.3 mm) to give 11.2 g (67% yield) of 1,1-dicyano-4-ethoxy-3-methyl-1,3-butadiene.

b. 1,1-Dicyano-4-ethoxy-3-methyl-1,3-butadiene (11.2 g) was cyclized using basically the same procedure as Example 1 b.; and 3.0 g (15% yield) of 2-bromo-3-cyano-5-methyl-pyridine, m.p.=109°–111°, were obtained.

The following table lists the Formula V intermediates which were prepared using the processes substantially as disclosed in Examples 1 and/or 2, as applicable.

TABLE 1

| Ex. | Process of Example | Starting Material | Formula V Product | Product Yield wgt - % | Product M.P. or B.P. (mm.Hg) |
|---|---|---|---|---|---|
| 3 | 1(a)(b)(c) | CH$_3$\C=C/CO$_2$Et, CH$_3$/ \CN | CH$_3$-pyridine-CF$_3$,Br | 5.2g-58% | 110°–112° C. (at 0.7) |
| 4 | 1(a)(b) | H\C=C/CN, C$_2$H$_5$/ \CN | CH$_3$-pyridine-CN,Br | 0.4g-5% | 109°–111° C. |
| 5 | 1(a)(b) | C$_6$H$_5$\C=C/CN, CH$_3$/ \CN | C$_6$H$_5$-pyridine-CN,Br | 3.8g-22% | 122°–125° C. |

TABLE 1-continued

| Ex. | Process of Example | Starting Material | Formula V Product | Product Yield wgt - % | Product M.P. or B.P. (mm.Hg) |
|---|---|---|---|---|---|
| 6 | 1(a)(b) | (C2H5)(CH3)C=C(CN)2 | 4-C2H5-pyridine-3-CN, 2-Br | 2.4g-16% | 64°-65° C. |
| 7 | 1(a)(b) | (C6H5)(C2H5)C=C(CN)2 | 4-C6H5-6-CH3-pyridine-3-CN, 2-Br | 0.15g-3% | 123°-124° C. |
| 8 | 2(a)(b) | (CH3)(CH3)C=C(CN)2 | 4-CH3-pyridine-3-CN, 2-Br | 1.0g-23% | 109°-111° C. |
| 9 | 2(a)(b) | (C2H5)(CH3)C=C(CN)2 | 4-CH3-6-CH3-pyridine-3-CN, 2-Br | 6.3g-29% | 93°-95° C. |
| 10 | 2(a)(b) | (C6H5)(C2H5)C=C(CN)2 | 4-C6H5-6-CH3-pyridine-3-CN, 2-Br | 5.7g-42% | 123°-124° C. |
| 11 | 2(a)(b) | thiophene-C(CN)2 (benzothiophene fused) | thieno-pyridine-CN, Br | 2.0g-15% | 128.5°-130.5° C. |
| 12 | 2(a)(b) | thienyl-C(CN)2 | thieno-pyridine-CN, Br | 3.4g-15% | 103°-105° C. |
| 13 | 2(a)(b) | (H)(C2H5)C=C(COOC2H5)(CN) | 6-CH3-pyridine-3-COOC2H5, 2-Br | 4.3g-40% | 114°-120° C.(0.4) |

The following examples illustrate the preparation of other intermediates of Formula V. Temperatures are °C.

EXAMPLE 14

5-Acetamido-2-Chloronicotinonitrile

A solution of 5-amino-2-chloronicotinonitrile (2.6 g, 0.017 m) and acetic anhydride (50 ml) was heated at reflux for 30 minutes. After cooling to 25°, the reaction mixture was poured into water, neutralized with saturated Na2CO3 solution and extracted with CH2Cl2. The organic layer was dried over Na2SO4, filtered and concentrated to dryness. The residue was recrystallized from benzene/hexane to yield 2.5 g (76% yield) of 5-acetamido 2-chloronicotinonitrile.

Substituting appropriate alkanoic acid anhydrides for acetic anhydride in Example 14, the corresponding alkanoylamino substituted nicotinonitrile is obtained.

EXAMPLE 15

2-Chloro-5-(1-pyrrolyl)nicotinonitrile

A solution of 5-amino-2-chloronicotinonitrile (5.0 g, 0.033 m), 2,5-dimethoxytetrahydrofuran (11 g, 0.085 m) and acetic anhydride (20 ml) was heated at reflux with stirring. After two hours, the solution was concentrated to dryness under reduced pressure (20 mm). The residue was triturated with CCl4 and filtered to yield 5.2 g (78% yield) of 2-chloro-5-(1-pyrrolyl)nicotinonitrile, m.p.=144°-146°.

EXAMPLE 16

2-Fluoro-3-nitro-5-trifluoromethylpyridine/2-chloro-3-nitro-5-trifluoromethylpyridine mixture A steel bomb was charged with 6-chloro-5-nitronicotinic acid (4.1 g, 0.02 m), SF4 (21 g) and HF (3.7 ml). The mixture was heated at 90° for eight hours. After cooling to 25°, the bomb was vented and the contents poured onto ice. The solution was neutralized with saturated Na2CO3 solution and extracted with CH2Cl2. The organic layer was dried over Na2SO4, filtered and the solution was distilled. A mixture of 2-chloro and 2-fluoro-3-nitro-5-trifluoromethylpyridine (3.3 g) was obtained by distillation at 198°-200° (760 mm).

EXAMPLE 17

2-Fluoro-3-amino-5-trifluoromethylpyridine/2-chloro-3-amino-5-trifluoromethylpyridine mixture a. To a solution of 6-chloro-5-nitronicotinic acid in acetic acid (240 ml) was added iron (20 g) and the mixture was heated with stirring on a steam bath. After 1½ hours, the mixture was filtered hot and washed with hot acetic acid. The filtrate was concentrated to dryness and the residue was treated with 10% NaOH, filtered and the pH adjusted to 2-3. The solid was filtered to yield 8.0 g (60% yield) of 5-amino-6-chloronicotinic acid.

b. A steel bomb was charged with 5-amino-6-chloronicotinic acid (8.0 g, 0.046 m), $SF_4$ (12 g) and HF (4.2 g). The mixture was heated at 120° for eight hours. After cooling to 25°, the bomb was vented and the contents poured onto ice. The solution was neutralized with saturated $Na_2CO_3$ and extracted with $CHCl_3$. The organic layer was dried over $Na_2SO_4$, filtered and concentrated to dryness. The residue was sublimed at 50°-65° at 1.4 mm to yield 4.4 g of a mixture of 2-chloro and 2-fluoro-3-amino-5-trifluoromethylpyridine.

EXAMPLE 18

2-Fluoro-3-(1-pyrrolyl)-5-trifluoromethyl pyridine/2-Chloro-3-(1-pyrrolyl)-5-trifluoromethylpyridine mixture A solution of the mixture (1.1 g) from Example 17 b., 2,5-dimethoxytetrahydrofuran (0.9 g, 0.007 m) and acetic acid (5 ml) was heated at reflux with stirring. After 1½ hours, the solution was cooled and poured into saturated $Na_2CO_3$ solution. The aqueous layer was extracted with $CHCl_3$ and the organic layer was dried over $Na_2SO_4$, filtered and concentrated to dryness. The residue was chromatographed on silica gel and the product eluted with 1:1 $CH_2Cl_2$:hexane to yield 0.65 g of a mixture of 2-chloro and 2-fluoro-3-(1-pyrrolyl)-5-trifluoromethylpyridine.

EXAMPLE 19

2-Chloro-3-fluoro-5-trifluoromethylpyridine

A steel bomb was charged with 6-chloro-5-fluoronicotinic acid (5.4 g, 0.03 m), $SF_4$ (32.4 g) and HF (5.6 ml). The mixture was heated at 120° for eight hours. After cooling to 25°, the bomb was vented and the contents poured onto ice. The solution was neutralized with saturated $Na_2CO_3$ solution and extracted with $CH_2Cl_2$. The organic layer was dried over $Na_2SO_4$, filtered and the solvent distilled off on a steam bath. The residue was distilled at 115° (760 mm) to yield 1.4 g (23% yield) of 2-chloro-3-fluoro-5-trifluoromethylpyridine.

EXAMPLE 20

2-Chloro-5-fluoro-3-trifluoromethylpyridine

A steel bomb was charged with 2-chloro-5-fluoronicotinic acid (4.5 g, 0.026 m), $SF_4$ (27 g) and HF (4.7 ml). The mixture was heated at 120° for eight hours. After cooling to 25°, the bomb was vented and the contents poured onto ice. The solution was neutralized with saturated $Na_2CO_3$ solution and extracted with $CH_2Cl_2$. The organic layer was dried over $Na_2SO_4$, filtered and the solvent distilled off on a steam bath. The residue was distilled at 125° (760 mm) to yield 3.2 g (23% yield) of 2-chloro-5-fluoro-3-trifluoromethylpyridine.

EXAMPLE 21

1-Propylidenemalononitrile

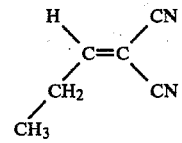

1-Propylidenemalononitrile (61.7 g b.p.=45 at 0.6 mm) was obtained from the reaction of malononitrile (50 g), propionaldehyde (47 g) acetic acid (10 ml), alanine (0.5 g) and benzene (140 ml) using the general procedure described by F. S. Prout in J. Org. Chem. 18, 928 (1953).

The following examples illustrate the preparation of the compounds of Formulae I and II. All temperatures are in °C.

EXAMPLE 22

(S) 4-Methyl-2-(3-tert butylamino-2-hydroxypropoxy)-3-trifluoromethylpyridine hydrogen maleate A dry flask was charged, under nitrogen, with (S) 2-phenyl-3-tert butyl-5-hydroxymethyloxazolidine (7.0 g, 0.03 m), dimethylformamide (DMF) (80 ml) and NaH (50% mineral oil, 1.3 g, 0.027 m) and heated, with stirring, at 90° for 30 minutes. After cooling to room temperature, 2-bromo-4-methyl-3-trifluoromethylpyridine (6.2 g, 0.026 m) in DMF (25 ml) was added and the mixture was stirred at 45°. After stirring overnight at 45°, the mixture was poured into saturated $Na_2CO_3$ (300 ml) and water (300 ml) and extracted with $Et_2O$ (4×300 ml). The organic layer was washed with water (2×300 ml) and cold 1 N HCl (3×200 ml). The acid layer was poured into sodium acetate .3$H_2O$ (82 g, 0.6 m) and the solution stirred at room temperature. After six hours, the solution was extracted with $Et_2O$ (2×250 ml). The aqueous layer was neutralized with saturated $Na_2CO_3$ and extracted with $CH_2Cl_2$ (4×200 ml). The organic layer was dried over $Na_2SO_4$, filtered and concentrated to dryness. The residue was chromatographed on silica gel 60 and product eluted with 20% $CH_3OH$—$CHCl_3$. The crude product was crystallized with maleic acid in isopropanol to give 0.8 g (8% yield) of (S) 4-methyl-2-(3-tert butylamino-2-hydroxypropoxy)-3-trifluoromethylpyridine hydrogen maleate, m.p.=126°-128° ($Et_2O$-isopropanol).

EXAMPLE 23

(S) 3-Cyano-4,5-dimethyl-2-(3-tert butylamino-2-hydroxypropoxy)pyridine hydrogen maleate A dry flask was charged, under nitrogen, with tert butanol (50 ml), potassium metal (0.58 g, 0.015 m), and (S) 2-phenyl-3-tert butyl-3-hydroxymethyloxazolidine (4 g, 0.017 m) and heated at 40° with stirring until all the potassium metal reacted. Then, 2-bromo-3-cyano-4,5-dimethylpyridine (3.0 g, 0.014 m) in tert butanol (5 ml) was added and the mixture heated at 70°. After heating overnight, the mixture was concentrated to dryness and stirred with water (150 ml) and acetic acid (9.0 g). After five hours, the solution was extracted with $Et_2O$ (2×100 ml). The aqueous layer was neutralized with saturated Na₂CO₃ and extracted with CHCl₃ (3×100 ml). The organic layer was dried over Na₂SO₄, filtered and concentrated to dryness. The residue was crystallized with maleic acid in isopropanol to give 4.1 g (75% yield) of (S) 3-cyano-4,5-dimethyl-2-(3-tert butylamino-2-hydroxypropoxy)pyridine hydrogen maleate, m.p.=148°-150° (Et₂O-isopropanol).

The free base may be obtained from the hydrogen maleate salt by conventional neutralization with an appropriate base. Other salts may be prepared from the free base by treating with an appropriate acid.

The following Table contains additional examples of the Formula I and II pyridines which are prepared using the appropriate Formula V intermediates in a procedure substantially as described in Examples 22 or 23.

TABLE 2

| Ex | Pyridine Intermediate | (S) Isomer Product① | % Yield | M.P.(°C.) |
|---|---|---|---|---|
| 24 | CH₃ / CN / Br | CH₃ / CN / O—β · HMal | 41 | 160–162 |
| 25 | F₃C / NO₂ / Cl/F Mix. | CF₃ / NO₂ / O—β · HCl | 8 | 176–178 |
| 26 | CH₃ / CN / Br | CH₃ / CN / O—β · HMal | 6 | 160–162 |
| 27 | N / CN / Cl | N / CN / O—β · HCl | 14 | 221–223 |
| 28 | CH₃ / CF₃ / Br | CH₃ / CF₃ / O—β · HMal | 8 | 126–128 |
| 29 | CH₃—C(O)—NH / CN / Cl | Ac—NH / CN / O—β · HMal | 4.5 | 98–100 |
| 30 | CH₃ / CF₃ / Cl | CH₃ / CF₃ / O—β · HMal | 8.6 | 149–151 |
| 31 | C₆H₅ / CN / Br | C₆H₅ / CN / O—β · HCl | 21 | 193–196 |
| 32 | CF₃ / F / Cl | CF₃ / F / O—β | 50 | 71–73 |
| 33 | CF₃ / N / Cl/F mix. | CF₃ / N / O—β · HMal | 23 | 129–130 |
| 34 | F / CF₃ / Cl | F / CF₃ / O—β · HMal | 16 | 101–103 |
| 35 | CH₃ / CH₃ / CN / Br | CH₃ / CH₃ / CN / O—β · HMal | 75 | 148–150 |

TABLE 2-continued

| Ex | Pyridine Intermediate | (S) Isomer Product ① | % Yield | M.P.(°C.) |
|---|---|---|---|---|
| 36 | 4-C₂H₅, 3-CN, 2-Br pyridine | 4-C₂H₅, 3-CN, 2-O–β pyridine · HMal | 56 | 123–125 |
| 37 | thiophene-fused pyridine with CN, Br | thiophene-fused pyridine with CN, O–β | 35 | 101 |
| 38 | thiopyran-fused pyridine with CN, Br | thiopyran-fused pyridine with CN, O–β | 53 | 54–56 |
| 39 | 4-C₆H₅, 5-CH₃, 3-CN, 2-Br pyridine | 4-C₆H₅, 5-CH₃, 3-CN, 2-O–β pyridine · HCl | 5 | 243–244 |
| 40 | 6-CH₃, 3-CN, 2-Cl pyridine | 6-CH₃, 3-CN, 2-O–β pyridine · HCl | 20 | 208–210 |
| 41 | 4-CH₃, 6-CH₃, 3-CN, 2-Cl pyridine | 4-CH₃, 6-CH₃, 3-CN, 2-O–β pyridine · HCl · ½H₂O | 22 | 177–178 |
| 42 | dioxolanyl-substituted pyridine with CN, Br | CHO-substituted pyridine with CN, O–β | | |
| 43 | HOCH₂-pyridine with CN, Br | HOCH₂-pyridine with CN, O–β | | |
| 44 | C₂H₅O₂C-pyridine with CN, Br | C₂H₅O₂C-pyridine with CN, O–β | | |
| 45 | HO₂C-pyridine with CN, Br | HO₂C-pyridine with CN, O–β | | |
| 46 | (C₂H₅O)₂CH-pyridine with CO₂C₂H₅, Br | CHO-pyridine with CO₂C₂H₅, O–β | | |
| 47 | HOCH₂-pyridine with CO₂C₂H₅, Br | HOCH₂-pyridine with CO₂C₂H₅, O–β | | |
| 48 | C₂H₅O₂C-pyridine with CO₂C₂H₅, Br | C₂H₅O₂C-pyridine with CO₂C₂H₅, O–β | | |

TABLE 2-continued

| Ex | Pyridine Intermediate | (S) Isomer Procuct[1] | % Yield | M.P.(°C.) |
|---|---|---|---|---|
| 49 | 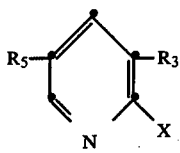 | HO₂C—[pyridine-O ring]—CO₂C₂H₅, —O—β | | |

[1] β = CH₂—CHOH—CH₂—NH—t-butyl;
HMal = hydrogen maleate;
HCl = hydrochloride.

While the Examples are directed to (S) isomers, the corresponding (R) isomer or (R/S) racemate is prepared by substituting the appropriate (R) or (R/S) oxazolidine for the (S) oxazolidine in the processes illustrated by Examples 22–39.

Another aspect of the present invention is a process for preparing useful pyridine intermediates of the formula $$R_5 \underset{N}{\underset{\parallel}{\bigcirc}} \underset{X}{\overset{R_3}{}} \qquad 2$$

when $R_3$ is CO₂Et or CN, $R_5$ is CHO or CO₂Et and X is Br. The process involves the reaction of a compound of the formula

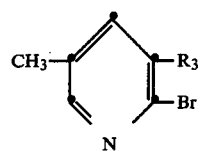

1 with N-bromosuccinimide (NBS) followed by appropriate hydrolysis. These processes are illustrated by the following reaction equations. Various substituent groups and group combinations are identified under the compound formulae in the equation with an individual number. These numbers are used to designate compounds described in the illustrative examples which follow the equations.

Equation Sequence A

$$H_3C \underset{N}{\bigcirc} \underset{Br}{\overset{R_3}{}} \xrightarrow[\text{CCl}_4 \text{ (PhCO}_2)_2]{\text{NBS/h}\gamma} R_5' \underset{N}{\bigcirc} \underset{Br}{\overset{R_3}{}}$$
(a) → (b)

| Compound No. | Formula (a) where |
|---|---|
| 4 | R₃ = CO₂Et |
| 9 | R₃ = CN |

$$R_5' \underset{N}{\bigcirc} \underset{Br}{\overset{R_3}{}} \xrightarrow[\text{EtOH—H}_2\text{O}]{\text{AgNO}_3} R_5 \underset{N}{\bigcirc} \underset{Br}{\overset{R_3}{}}$$
(b) → (c)

| Compound No. | Formula (b) where | Compound No. | Formula (c) where |
|---|---|---|---|
| 5 | R₃ = CO₂Et; R₅' = CH₂Br | 3 | R₃ = CO₂Et; R₅ = CHO |
| 6 | R₃ = CO₂Et; R₅' = CHBr₂ | 8 | R₃ = R₅ = CO₂Et |
| 7 | R₃ = CO₂Et; R₅' = CBR₃ | 13 | R₃ = CN; R₅ = CHO |
| 10 | R₂ = CN, R₅' = CH₂Br | 14 | R₃ = CN; R₅ = CH⟨O—X / O—⟩ |
| 11 | R₃ = CN; R₅' = CHBr₂ | 15 | R₃ = CN; R₅ = CO₂Et |
| 12 | R₃ = CN; R₅' = CBr₃ | 16 | R₃ = CN; R₅ = CO₂H |
| | | 21 | R₃ = CO₂Et; R₅ = CH⟨OC₂H₅ / OC₂H₅⟩ (X) |
| | | 22 | R₃ = CO₂Et; R₅ = CH₂OH |
| | | 23 | R₃ = CN; R₅ = CH₂OH |

| | 24 | $R_3 = CO_2Et$; $R_5 = CO_2H$ |

$^x$ This $R_5$ acetal group is derived from the formyl group by an additional step using conventional method of acetal formation; see e.g. Examples 56 and 60.

The following Examples illustrate the Equation Sequence A reaction. All temperatures are in degrees Celsius.

EXAMPLE 50

Ethyl 2-bromo-5-dibromomethylnicotinate (6)

A mixture or 4 (24.1 g, 0.1 mol), NBS (40 g, 0.22 mol), CCl$_4$ (500 mL) and dibenzoyl peroxide (1.0 g) was heated at reflux while being illuminated by a 275 W sun lamp. After 24 hours, the reaction mixture was filtered and concentrated to dryness. The residue was crystallized from ligroin to yield 14 g (35%) of 6. Recrystallization of a small sample from ligroin gave 6 of mp 88°–89° C.; $^1$H NMR (CDCl$_3$) 1.45 δ (3H, t, J=7), 4.45 (2H, q, J=7), 6.7 (1H, s), 8.1 (1H, d, J=2) and 8.4 (1H, d, J=2).

The mother liquor from the crystallization was concentrated to dryness and the residue chromatographed on silica gel. Elution with CHCl$_3$ gave 2.7 g (6%) of 7 and 13.1 g of a 1:1 mixture of 5 and 6 as determined by $^1$H NMR spectroscopy.

EXAMPLE 51

Ethyl 2-bromo-5-tribromomethylnicotinate (7)

A mixture of 4 (5.4 g, 0.022 mol), NBS (13 g, 0.073 mol), CCl$_4$ (150 mL) and dibenzoyl peroxide (0.2 g) was illuminated by a 275 W sun lamp for 24 hours. Additional NBS(5 g) was then added and illumination continued for another 24 hours. After cooling to 25°, the mixture was filtered and concentrated to dryness. The residue was chromatographed on silica gel and eluted with 25% C$_6$H$_{14}$—CHCl$_3$ to yield 5.1 g (49%) of 7 and 1.2 g (13%) of 6. An analytical sample of 7 was prepared by crystallization from ligroin, mp 50°–52° C.; $^1$H NMR (CDCl$_3$) 1.4 δ (3H, t, J=7), 4.4 (2H, q, J=7), 8.4 (1H, d, J=2) and 8.8 (1H, d, J=2).

EXAMPLE 52

Ethyl 2-bromo-5-formylnicotinate (3)

A mixture of 6 (9.8 g, 0.024 mol), AgNO$_3$ (8.8 g, 0.052 mol), EtOH (100 mL) and H$_2$O (25 mL) was heated on a steam bath for 1 hour. The yellow solid was filtered and the solution concentrated to dryness. The residue was treated with H$_2$O and extracted with CHCl$_3$ (3×). The organic layer was dried, filtered and concentrated to dryness. Distillation of the resulting oil at 105°–135° C. at 0.5 mm gave 3.0 g (48%) of 3; $^1$H NMR (CDCl$_3$) 1.45 δ (3H, t, J=7), 4.4 (2H, q, J=7, 8.6 (1H, d, J=2),/8.9 (1H, d, J=2) and 10.1 (1H, s).

EXAMPLE 53

Diethyl 2-bromo-3,5-pyridinedicarboxylate (8)

A mixture of 7 (2.3 g, 0.005 mol), AgNO$_3$ (2.5 g, 0.015 mol) and EtOH (25 mL) was heated on a steam bath. After 1 hour, H$_2$O (25 mL) was added and the yellow solid filtered off. The solution was concentrated to dryness and the residue treated with H$_2$O and extracted with CHCl$_3$ (3×). The CHCl$_3$ layers were washed with NaHSO$_3$ solution, dried, filtered and concentrated to dryness to yield 0.8 g (78%) of 8; $^1$H NMR (CDCl$_3$) 1.4 δ (6H, t, J=7), 4.45 (4H, q, J=7), 8.6 (1H, d, J=3) and 9.0 (1H, d, J=3).

EXAMPLE 54

2-Bromo-5-dibromomethylnicotinonitrile (11) and 2-Bromo-5-tribromomethylnicotinonitrile (12)

A mixture of 9 (10 g, 0.05 mol), NBS (20 g, 0.11 mol), CCl$_4$ (500 mL) and dibenzoyl peroxide (0.5 g) was heated at reflux while being illuminated by a 275 W sun lamp for 7 hours. After allowing to stand overnight at room temperature, the mixture was filtered and concentrated to dryness. The residue was chromatographed on silica gel and the products eluted with 50% C$_6$H$_{14}$—CHCl$_3$. There was obtained 3.8 g (18%) of 12 and 8.3 g (47%) of 11. An analytical sample of 11 was prepared by crystallization from CH$_2$Cl$_2$—C$_6$H$_{14}$, mp 89°–90° C.; $^1$H NMR (CDCl$_3$) 6.6 δ (1H, s), 8.15 (1H, d, J=3) and 8.7 (1H, d, J=3).

An analytical sample of 12 was prepared by crystallization from logroin, mp 120°–31° C.; $^1$H NMR (CDCl$_3$) 8.3 δ (1H, d, J=3) and 9.1 (1H, d, J=3); IR (nujol) 2270 and 1740 cm$^1$.

EXAMPLE 55

2-Bromo-5-formylnicotinonitrile (13)

A mixture of 9 (2.1 g, 0.006 mol), AgNO$_3$ (2.2 g, 0.013 mol), EtOH (25 mL) and H$_2$O (5 mL) was heated on a steam bath for 1 hour. After filtering off the yellow solid, the solution was concentrated to dryness. The residue was treated with H$_2$O and extracted with CHCl$_3$ (3×). The organic layer was dried, filtered and concentrated to dryness. The residue was treated with acetone —H$_2$O (10:1) and a few drops of 12 N NCl. After heating on a steam bath for 1 hour, the solution was poured into saturated Na$_2$CO$_3$ and extracted with Et$_2$O (3×). The organic layer was dried, filtered and concentrated to dryness to yield 0.9 g (75%) of 13 mp 105°–6° C. (ligroin); $^1$H NMR (CDCl$_3$) 8.4 δ (1H, d, J=2), 9.0 (1H, d, J=2) and 10.1 (1H, s).

EXAMPLE 56

2-Bromo-5-formylnicotinonitrile ethylene glycol acetal (14)

A mixture of 13 (0.8 g, 0.004 mol), C$_6$H$_6$ (50 mL), ethylene glycol (1 mL) and p-TsOH (0.1 g) was heated on a steam bath with the continual removal of H$_2$O using a Dean-Stark trap. After 2 hours, the solution was cooled and washed with saturated Na$_2$CO$_3$ solution. After separation, the aqueous layer was further extracted with Et$_2$O (2×). The combined organic extracts were dried, filtered and concentrated to dryness to yield 1.0 g (100%) of 14, mp 74°–75° C. (ligroin); $^1$H NMR (CDCl$_3$) 4.05 (4H, s), 5.85 (1H, s), 8.05 (1H, d, J=3) and 8.65 (1H, d, J=3).

EXAMPLE 57

Ethyl 6-bromo-5-cyanonicotinate (15)

A mixture of 12 (1.4 g, 0.003 mol), AgNO$_3$ (1.7 g, 0.01 mol), EtOH (25 mL) and H$_2$O (5 mL) was heated on a steam bath for 1½ hours. After filtering off the yellow solid, the solution was concentrated to dryness to yield 0.6 g (79%) of 15. An analytical sample was prepared by crystallization from EtOH-H₂O mp 92°–93° C.; ¹H NMR (CDCl₃) 1.35 δ (3H, t, J=7), 4.35 (2H, q, J=7), 8.7 (1H, d, J=3) and 8.8 (1H, d, J=3).

EXAMPLE 58

6-Bromo-5-cyanonicotinic acid (16)

A mixture of 12 (2.0 g, 0.004 mol), AgNO₃ (2.2 g. 0.014 mol), H₂O (40 mL) and EtOH (8 mL) was heated on a steam bath for 2 hours. The mixture was then poured into saturated Na₂CO₃, filtered and extracted with CHCl₃ (2×). The aqueous layer was acidified with 12 N HCl and extracted with Et₂O (3×). The Et₂O layer was dried, filtered and concentrated to dryness to yield 0.7 g (74%) of 16, mp 170°–172° C. (EtOH-H₂O); ¹H NMR (DMSO-d₆) 8.8 δ (1H, d, J=2) and 9.15 (1H, d, J=2); (nujol) 2270 and 1725 cm⁻¹.

EXAMPLE 59

5-Formylnicotinonitrile ethylene glycol acetal (17)

A mixture of 14 (1.0 g, 0.004 mol), EtOH (75 mL), H₂O (40 mL), MgO (1 g) and 5% Pd/C (1 g) was placed on a Herschberg hydrogenation apparatus. After 100 mL of H₂ was absorbed (~10 min), the suspension was filtered under a blanket of N₂ and the volatiles removed under reduced pressure. The resulting residue was treated with H₂O and extracted with CHCl₃ (3×). The combined organic extracts were dried, filtered and concentrated to dryness to yield 0.7 g (100%) of 17. An analytical sample of 17 was prepared by sublimation at 65° C. at 0.2 mm, mp 73°–5° C.; ¹H NMR (CDCl₃) 4.1 δ (4H, s), 5.9 (1H, s), 8.03 (1H, t) and 8.83 (2H, bs); IR (nujol) 2250 cm⁻¹.

EXAMPLE 60

Ethyl 2-bromo-5-formylnicotinate diethyl acetal (21)

A mixture of 3 (2.58, 0.01 mol), HC(OEt)₃ (1.7 g, 0.011 mol), absolute EtOH (20 ml) and concentrated H₂SO₄ (3 drops) is heated on a steam bath. After 18 hours, the solution is poured into saturated NaHCO₃ and extracted with CHCl₃ (3×). The organic layer is dried, filtered and concentrated to dryness to yield 21.

EXAMPLE 61

Ethyl 2-bromo-5-hydroxymethylnicotinate (22)

Compound 22 is prepared from 5 in a manner similar to the preparation of 3 except a slight excess over one equivalent of AgNO₃ is used.

EXAMPLE 62

2-Bromo-5-hydroxymethylnicotinonitrile (23)

Compound 23 is prepared from 10 in a manner similar to the preparation of 13 except a slight excess over one equivalent of AgNO₃ is used.

EXAMPLE 63

6-Bromo-5-carboethoxynicotinic acid (24)

Compound 24 is prepared from 7 in a manner similar to the preparation of 16.

EXAMPLE 64

(S) Ethyl 2-(3-tert butylamino-2-hydroxypropoxy)-5-hydroxymethyl-nicotinate

Step A

To a cold solution of 22 (1.8 g, 0.01 mol), Et₂O (25 ml) and Et₃N (1.0 g, 0.01 mol) is added dropwise with stirring trimethylsilyl chloride (1.1 g, 0.01 mol). After the addition, the mixture is stirred at 25° for 1 hour and then the solid is filtered off. The resulting solution is concentrated to dryness and this product is used directly in the next step.

Step B

The product from step A is dissolved in DMF (10 ml) and used as described in Example 22 to yield the (S) ethyl 2-(3-tert butylamino-2-hydroxypropoxy)-5-hydroxymethylnicotinate compound.

EXAMPLE 65

(S) 2-(3-tert butylamino-2-hydroxypropoxy)-5-hydroxymethyl-nicotinonitrile (S) 2-(3-tert butylamino-2-hydroxypropoxy)-5-hydroxymethylnicotinonitrile is prepared from 23 in a manner similar to the preparation of (S) ethyl 2-(3-tert-butylamino-2-hydroxypropoxy)-5-hydroxymethyl-nicotinate in Example 64.

Where X in compound 2 is H, the compound is prepared by reductive dehalogenation of the corresponding Br compound. This is illustrated by the following equations.

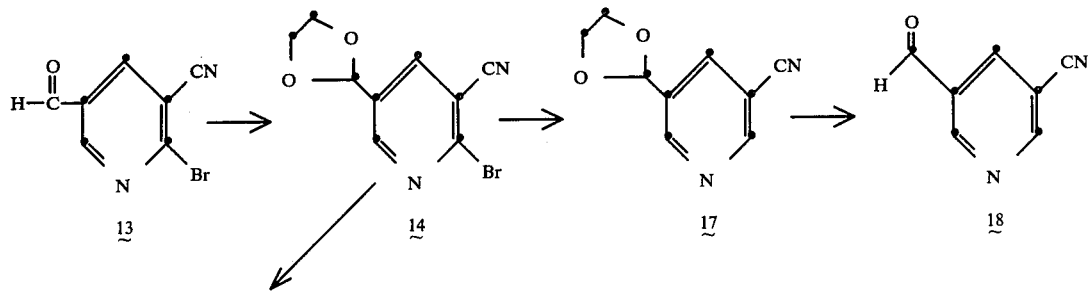

EQUATION B

-continued
EQUATION B

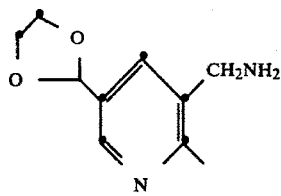

The following examples demonstrate the Equation B processes. All temperatures are in degrees Celsius.

EXAMPLE 66

5-Formylnicotinonitrile (18)

A solution of 17 (0.25 g, 0.0014 mol) in 1 N HCl (30 mL) was heated on a steam bath for 45 min. After cooling, the solution was poured into saturated $NaHCO_3$ and extracted with $CH_2Cl_2$ (3×). The combined organic layers were dried, filtered and concentrated to dryness to yield 0.16 g (89%) of 18. An analytical sample of 18 was prepared by crystallization from $CH_2CL_2-C_6H_{14}$, mp 96°–98° C.; $^1$H NMR ($CDCl_3$) 8.35 δ (1H, t), 8.97 (1H, d, J=2), 9.2 (1H, d, J=2) and 10.07 (1H, t); IR (nujol) 2250 and 1700 $cm^{-1}$.

EXAMPLE 67

3-Aminomethyl-5-formylpyridine ethylene glycol acetal (19)

A mixture of 14 (1.0 g, 0.004 mol), EtOH (75 mL) and 5% Pd on $CaCO_3$ (1 g) was placed on a Herschberg hydrogenation apparatus. After 340 mL of $H_2$ were absorbed the reaction was stopped. The mixture was filtered under a blanket of $N_2$ and the filtrate concentrated to dryness. The residue was chromatographed on silica gel and the product eluted with $CHCl_3$ saturated with $NH_3$ to yield 0.34 g (50%) of 19; $^1$H NMR ($CDCl_3$) 2.5 δ (2H, s), 3.8 (2H, exch), 4.0 (4H, s), 5.75 (1H, s), 7.7 (1H, bs) and 8.4 (2H, bs); IR (neat) 3330 $cm^{-1}$; MS (M+) 180.

Claims to the invention follow.
What is claimed is:
1. A compound having the formula

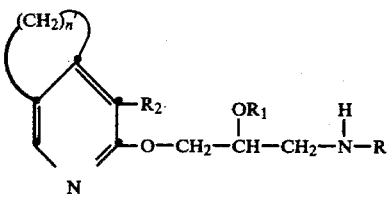

wherein
n' is 3 or 4,

R is $C_3$–$C_4$ branched alkyl,
$R_1$ is H or

wherein L is selected from $C_1$–$C_{10}$ alkyl, phenyl and substituted phenyl having up to two substituents which are independently selected from $C_1$–$C_4$ alkyl, $C_1$–$C_4$ alkoxy and halo, and
$R_2$ is CN,
and pharmaceutically acceptable salts thereof.
2. Compound of claim 1 having the S-isomer configuration.
3. Compound of claim 1 wherein $R_1$ is H.
4. A compound of claim 1 wherein $R_1$ is H and R is isopropyl or t-butyl.
5. A compound of claim 4 wherein n' is 3.
6. A compound of claim 4 wherein n' is 4.
7. A compound of claim 1 having the formula

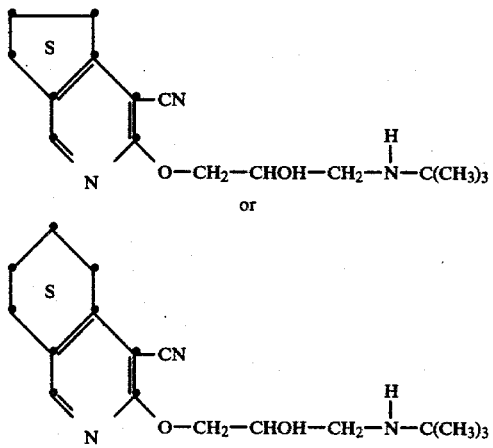

8. A pharmaceutical composition for effecting β-adrenergic blockade containing an effective amount of a compound of claim 1 and a diluent.
9. A pharmaceutical composition for treating hypertension containing an effective amount of a compound of claim 1 and a diluent.

* * * * *